US00PP23188P3

(12) United States Plant Patent
Geibel

(10) Patent No.: US PP23,188 P3
(45) Date of Patent: Nov. 13, 2012

(54) **VARIETY OF *PELARGONIUM* PLANT NAMED 'PACNEAMEX'**

(50) Latin Name: *Pelargonium peltatum*
Varietal Denomination: Pacneamex

(75) Inventor: Martin Geibel, Dresden (DE)
(73) Assignee: Elsner pac Jungpflanzen, Dresden (DE)

( * ) Notice: Subject to any disclaimer, the term of this patent is extended or adjusted under 35 U.S.C. 154(b) by 0 days.

(21) Appl. No.: 13/066,405

(22) Filed: Apr. 14, 2011

(65) Prior Publication Data

US 2012/0266341 P1 Oct. 18, 2012

(51) Int. Cl.
*A01H 5/00* (2006.01)

(52) U.S. Cl. ..... Plt./332

(58) Field of Classification Search ..... Plt./332
See application file for complete search history.

*Primary Examiner* — Kent L Bell
(74) *Attorney, Agent, or Firm* — The Webb Law Firm

(57) ABSTRACT

'Pacneamex' is a new variety of ivy *pelargonium* having a trailing growth habit, strong vigor, double and bi-colored magenta and white flowers.

1 Drawing Sheet

Botanical classification: *Pelargonium peltatum.*
Varietal denomination: 'Pacneamex'.

BACKGROUND OF THE INVENTION

The present invention comprises a new and distinct cultivar of *Pelargonium peltatum* known by the varietal name 'Pacneamex'. The new variety was discovered in Dresden, Germany in the Summer of 2006. The new variety is a result of a planned breeding program using the following procedure: a bulk of different genotypes were crossed to obtain big, double flowers with a magenta color and good heat resistance; cuttings of *pelargonium* seedling 'Pennea' (U.S. Plant Patent Application Publication No. 2002/0073470, abandoned) having the best flowering characteristics and best growth habit were grown onto *pelargonium* variety 'Pactomgimex' (U.S. Plant Pat. No. 13,783) to transfer its bi-colored stripe pattern; when the grafted tips flowered bi-colored, cuttings were made and plants of the resulting striped new variety were tested for over three years; and, the most stable plant was selected as the new variety, 'Pacneamex'. The purpose of the breeding program was to develop bi-colored, double flowering ivy *pelargoniums* with a stable flower pattern. 'Pacneamex' has bi-colored upper surface flower petals, while 'Pennea' has single-colored upper surface flower petals. The new variety exhibits a trailing habit, a bi-colored flower type, and all season flowering like 'Pactomgimex'. However, 'Pacneamex' has magenta-white flowers, while 'Pactomgimex' has red-white flowers. Further, the new variety is more vigorous and has more petals than 'Pactomgimex'. The new variety was first asexually reproduced by cuttings in the Summer of 2006 in Dresden, Germany. The new variety has been trial and field tested and has been found to retain its distinctive characteristics and remain true to type through successive propagations.

The new variety was grown in a greenhouse in a 19 cm pot in Dresden, Germany using four applications of cycocel 720, 0.2%. The new variety was pinched twice during development. The new variety has a response time of twelve weeks from a rooted cutting to flowering in a 12 cm container.

The following characteristics have been repeatedly observed and are determined to be unique characteristics that distinguish 'Pacneamex' as a new and distinct cultivar from others known to the breeder:

1) Stable, bi-colored flowers;
2) Big, double flowers;
3) Strong vigor;
4) Good trailing habit;
5) All season flowering; and
6) Good heat stability.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out in Dresden, Germany. The color readings were taken indoors in a room with a window with no direct sunlight or artificial light. The new variety was nine months from a rooted cutting when described. Color references are primarily to The 1995 R.H.S. Colour Chart of The Royal Horticultural Society of London.

PLANT

Market class: Ivy.
Time to initiate roots: About 21 days at about 18-20° C.
Time to develop roots: About 28 days at about 18-20° C.
Rooting habit: Freely branching roots.
Form: Trailing.
Height from media surface to top of foliage: 23 cm.
Height from media surface to top of flowers: 27 cm.
Strength (need for artificial support): Long branches need support during production.
Branching habit: Freely branching.

Plant diameter: 50 cm.
Vigor: Very high.
Stem:
*Main stem length.*—30-50 cm.
*Diameter.*—5 mm.
*Color.*—144A to 148A.
*Texture.*—Rough.
*Pubescence.*—Medium.
*Internode length.*—2-5 cm.
Lateral branches:
*Length.*—Primary: 20-40 cm. Secondary: 2-10 cm.
*Diameter.*—Primary: 4 mm. Secondary: 3 mm.
*Internode length.*—25 mm.
*Texture.*—Rough.
*Pubescence.*—Medium.
*Color.*—144A to 148A.
Foliage:
*Arrangement.*—Mainly opposite, sometimes alternate.
*Stipules.*—Size: Length: 6 mm. Width: 4 mm. Color: 146A.
*Zone.*—Location: 2 cm from margin. Color: 200B on young leaves, not present on older leaves.
*Size of leaf.*—Length: 4 cm. Width: 6 cm.
*Shape of leaf (generally).*—Ivy shaped.
*Shape of apex.*—Cuneate.
*Shape of base.*—Open and sometimes grown together near the petiole.
*Texture.*—Rough and leathery.
*Aspect.*—Glossy.
*Margin type.*—Entire.
*Pubescence.*—Upper surface: Light. Lower surface: Very light.
*Color.*—Young leaves: Upper surface: 146A to 147A. Lower surface: 146A. Mature leaves: Upper surface: 146A to 147A. Lower surface: 146A.
*Petiole.*—Length: 25-30 mm. Diameter: 2 mm. Color: 146A.
*Veins.*—Venation type: Palmate. Color: Upper surface: 146B. Lower surface: 146B.

INFLORESCENCE

Bud:
*Stage of development when bud characteristics determined.*—Before color appears.
*Shape of cluster.*—Bell-shaped.
*Diameter of cluster.*—3 cm.
*Number of buds per cluster.*—7.
*Shape of individual bud.*—Spindle-shaped.
*Length of individual bud.*—12 mm.
*Width of individual bud.*—6 mm.
Natural flowering season: Spring until frost in moderate climates.
Blooming habit: Continuous and early blooming.
Umbel diameter: 8 cm.
Umbel depth: 5 cm.
Borne: Umbel, flowers on pedicel, pedicel on peduncle.
Inflorescence position: Above foliage.
Number of inflorescences per lateral branch: About 3 at the same time.
Lastingness of an individual flower: 6-10 days.

Florets:
*Form.*—Flat.
*Number per umbel.*—5.
*Diameter.*—55 mm.
*Depth.*—20 mm.
Petals:
*Color.*—Upper surface: Margin and stripes 67B, middle areas 76D. Lower surface: 76D with a margin of 67B, stripes rarely present.
*Shape.*—Spoon-like.
*Length.*—25 mm.
*Width.*—17 mm.
*Apex shape.*—Round.
*Base shape.*—Pointed.
*Margin.*—Entire.
*Number per floret.*—23.
*Texture.*—Velvety.
*Tonality from a distance.*—Bi-colored violet/white.
Petaloids:
*Presence.*—If present, 1-2.
*Shape.*—Irregular.
*Color.*—Upper surface: Margin and stripes 67B, middle areas 76D. Lower surface: 76D with a margin of 67B, stripes rarely present.
*Length.*—10 mm.
*Width.*—4 mm.
Pedicel:
*Length.*—22 mm.
*Diameter.*—2 mm.
*Color.*—144A.
Peduncle:
*Length.*—11 cm.
*Diameter.*—3 mm.
*Texture.*—Sticky, a little bit rough.
*Color.*—144A.
Fragrance: None present.
Disease resistance: None observed to date.
Temperature tolerance: Good heat stablility.
Drought tolerance: Average.

REPRODUCTIVE ORGANS

Stamens:
*Number (per flower).*—3-5.
*Filament.*—Length: 10 mm. Color: White.
*Anthers.*—Shape: An elongated short tube. Length: 2 mm. Color: 176B.
*Pollen.*—Color: 167A. Amount (generally): Plentiful.
Pistils:
*Number.*—1.
*Length.*—10 mm.
*Style.*—Length: 2 mm. Color: White.
*Stigma.*—Shape: Actinomorphic, 5-7 parted. Color: 67A. Size: 5 mm.
*Ovaries.*—Pubescence: Present. Length: 3 mm. Width: 2 mm. Color: 138D.

I claim:

1. A new and distinct variety of *pelargonium* plant named 'Pacneamex' as is herein described and illustrated.

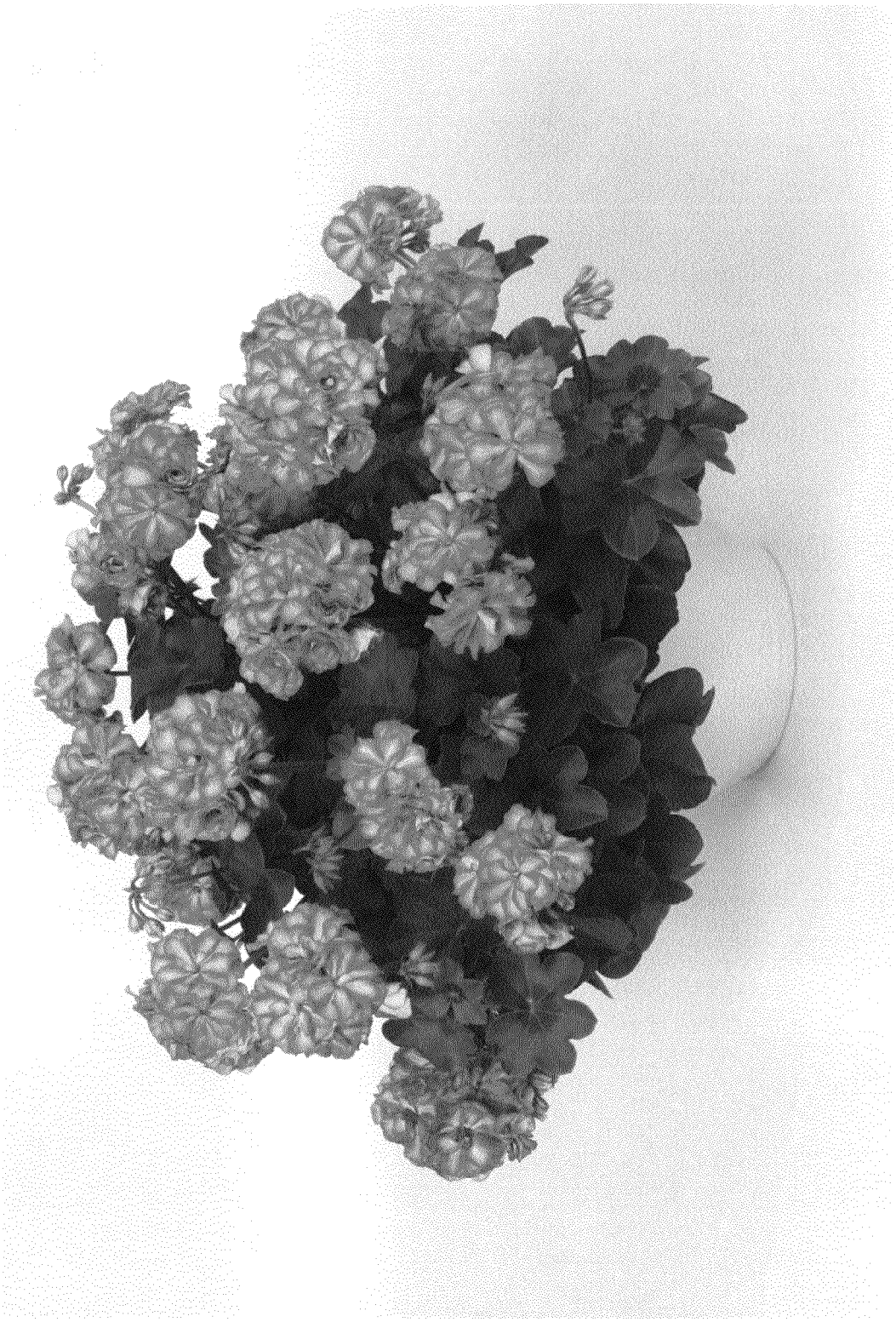

* * * * *